United States Patent [19]

Wilk

[11] Patent Number: 4,950,285

[45] Date of Patent: Aug. 21, 1990

[54] SUTURE DEVICE

[76] Inventor: Peter J. Wilk, 185 W. End Ave., New York, N.Y. 10023

[21] Appl. No.: 441,314

[22] Filed: Nov. 27, 1989

[51] Int. Cl.$^5$ ..................... A61B 17/00; B65D 63/00
[52] U.S. Cl. ..................... 606/232; 606/224; 606/151; 24/16 PB; 24/17 AP
[58] Field of Search ............... 606/232, 233, 228, 151, 606/139, 224; 24/16 PB, 30.5, 17 AP

[56] References Cited

U.S. PATENT DOCUMENTS

| | | | |
|---|---|---|---|
| 1,848,318 | 3/1932 | Ciampi | 24/713 |
| 3,072,986 | 1/1963 | Lefnaer | 24/16 PB |
| 3,570,497 | 3/1971 | Lemole | 606/228 |
| 3,597,803 | 8/1971 | Van Neil | 24/16 PB |
| 3,625,220 | 12/1971 | Engelsher | 606/233 |
| 3,831,608 | 8/1974 | Kletschka et al. | 606/233 |
| 3,985,138 | 10/1976 | Jarvik | 606/231 |
| 4,038,725 | 8/1977 | Keefe | 24/16 PB |
| 4,069,825 | 1/1978 | Akiyama | 606/174 |
| 4,741,330 | 5/1988 | Hayhurst | 606/86 |
| 4,813,416 | 3/1989 | Pollak et al. | 606/151 |

FOREIGN PATENT DOCUMENTS

| | | | |
|---|---|---|---|
| 2301717 | 9/1976 | France | 24/16 PB |
| 903599 | 8/1962 | United Kingdom | 24/30.5 P |

Primary Examiner—Randall L. Green
Assistant Examiner—Gary Jackson
Attorney, Agent, or Firm—Coleman & Sudol

[57] ABSTRACT

A suture device comprises a body member formed with an aperture and an access channel extending from the aperture to an opening defined by a loop attached to one side of the body member. A thread connected to a side of the body member opposite the loop is provided along a portion of its length with a series of tapered projections. Protuberances are provided on the body member along the access channel for preventing a return of the thread through the channel upon a passing of the thread through the loop and subsequently through the channel into the aperture. The loop and the thread are cut at the body member upon the tightening of the thread about a blood vessel, other tubular duct or a cut in a body tissue or organ.

26 Claims, 4 Drawing Sheets

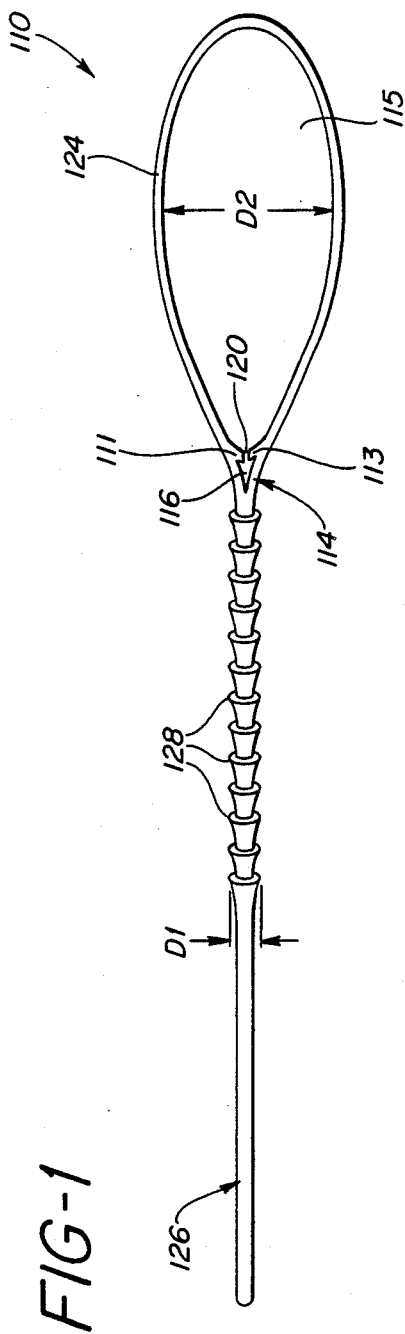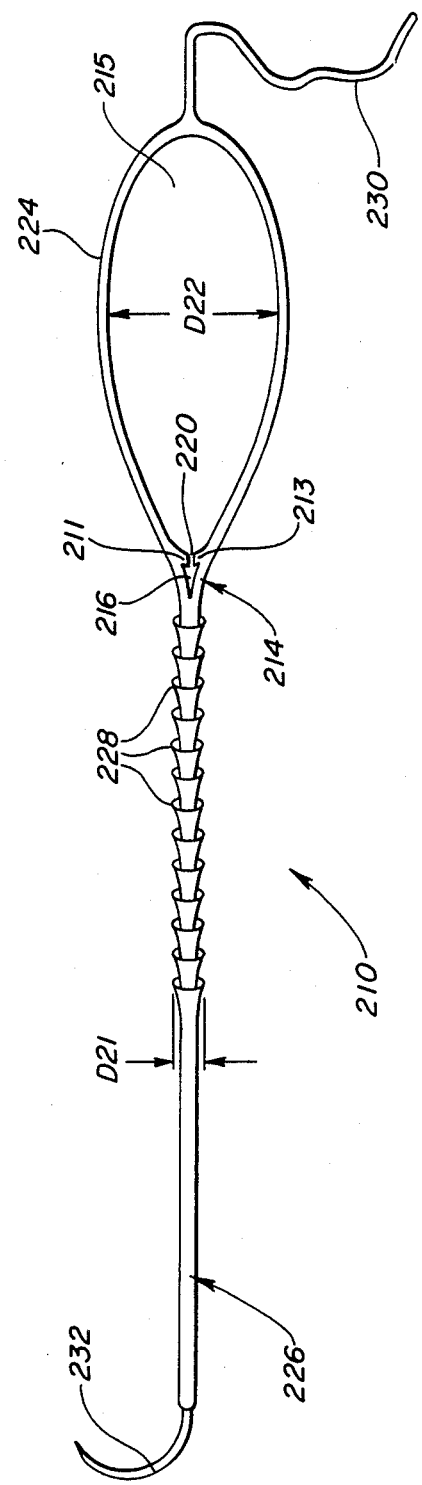

SUTURE DEVICE

BACKGROUND OF THE INVENTION

This invention relates to a suture device. More particularly, this invention relates to a suture device with components for locking the suture upon the application thereof at a surgical site.

As described in U.S. Pat. No. 3,570,497 to Lemole, a suture apparatus includes a cord of latch notches, a needle at one end of the cord, and a latch collar at the other end of the cord. The latch collar is provided with a passage through which the needle is pulled, followed by a selected number of latch notches. Upon the pulling of a final notch through the collar passage, the cord is severed on a side of the latch collar opposite the side of entry of the cord into the latch passage.

Although the suture device of U.S. Pat. No. 3,570,497 provides a number of advantages over simple suture threads, that suture device has several shortcomings which make it unsuitable for many surgical applications. Particularly in cases requiring fine stitches or ligatures, where the device of Lemole is necessarily small, the needle and cord of that device are inserted through the passage in the latch collar only with appreciable difficulty. Although in some applications, such as in the binding of a sternum or the approximating of ribs, a large suture device is necessary to provide the requisite strength, in other applications complications may arise by leaving a large suture structure at the surgical site.

U.S. Pat. No. 4,069,825 to Akiyama discloses a ligature including a surgical thread with a plurality of spherical or conical projections spaced regularly along the length of the thread. One end of the thread is attached to a cylindrical member having an aperture with a diameter larger than the outside diameter of the projections on the thread. The spacings between the projections and the size of the apertured member are designed to enable a locking of the thread in a loop about a vessel by means of friction forces which arise between the projections and the apertured member upon a passing of the thread through the aperture and a subsequent tightening of the loop so formed.

The ligature disclosed in Akiyama suffers from the same disadvantages as the suture device of Lemole. Basically, in cases where fine blood vessels or other ducts are to be closed, the passing of the thread through the apertured member is difficult and requires considerable concentration and patience.

As depicted in U.S. Pat. No. 3,985,138 to Jarvik, another ligature comprises an endless loop formed with a continuous series of ratchet-like ridges or pawl-like teeth. One side of the loop is connected via an elongate extension to a finger engaging loop, the extension traversing an opening in a closure member. Upon a pulling of the ridged loop through the closure by means of the finger engaging loop, the ridged loop is constricted and the teeth along the endless loop are caught against the closure to lock the endless loop in its constricted configuration.

Although the ligature of Jarvik obviates the problem of passing a thread through a small opening, the endless ridged or toothed loop must generally be passed over the end of a hemostat prior to closure of that loop about a severed blood vessel. This step clearly complicates the ligation procedure. In addition, the closure of the Jarvik ligature is necessarily bulky.

OBJECTS OF THE INVENTION

An object of the present invention is to provide a suture device of the above-described general type which can be used in both ligating and suturing operations.

Another object of the present invention is to provide such a suture device which is easy to use, even in cases requiring a small sutures or ligatures.

Another, more particular, object of the present invention is to provide such a suture device which is easy and inexpensive to manufacture.

A further particular object of the present invention is to provide such a suture device which comprises a reduced amount of material.

SUMMARY OF THE INVENTION

A suture device in accordance with the present invention comprises a thread member, a loop member, a connector element or portion, and a locking component or components. The thread member is provided along at least a portion of its length with a series of resilient projections and has an outer diameter defined by the projections. The loop member defines an opening having an effective linear dimension or diameter (when the loop is in a circular configuration) substantially larger than the outer diameter of the thread member, while the connector element serves to couple one end of the thread member to the loop member. Either the thread member or the connector element or both define at least in part an aperture having a linear dimension smaller than the outer diameter of the thread member, the aperture communicating with the opening in the loop member. The locking component or components are provided on either the connector element or the loop member or both and serve to prevent a removal of the thread member from the aperture upon a passing of the thread member through the loop member and a subsequent pulling of the thread member into the aperture from the loop member.

In using a suture device in accordance with the invention, a surgeon passes a free end of the thread member through or around a body tissue or organ to be sutured or ligated. Subsequently, the free end of the thread is passed through the loop member so that the thread member forms another loop. The surgeon then pulls the thread member through the loop member so that the thread member passes the locking component(s) into the aperture and so that the loop formed by the thread contracts. Upon the surgeon's continuing to pull the thread member through the aperture, the thread loop is tightened about the body tissue or organ to be sutured or ligated. The locking components automatically prevent the thread member from being withdrawn from the aperture. Finally, upon a completing of the pulling operation, the loop member and a free end portion of the thread member are severed from the connector element or body member. The protuberances may be disposed across an access channel from one another or may be staggered along the channel, the channel communicating with the aperture.

Pursuant to further features of the present invention, a locking component is in the form of a protuberance on the loop and projects towards the aperture. Preferably, there are two locking components in the form of two protuberances projecting from the loop towards the aperture.

Pursuant to another feature of the present invention, the connector element comprises a Y-shaped connector piece between the thread member and the loop member.

Pursuant to yet another feature of the present invention, the loop member is provided on a side opposite the connector element and the thread member with an extension such as an additional thread member. This extension facilitates the positioning of the loop member to receive the thread member. A surgeon uses the thread to hold the loop member out and away from the body tissues being sutured or ligated.

In accordance with a preferred embodiment of the present invention, the aperture is generally triangular.

In accordance with another, particular embodiment of the present invention, the connector element comprises a body member between the loop member and the thread member, the body member being formed with the aperture. In a preferred form, the body member is cylindrical, while the aperture is star-shaped.

Pursuant to yet further features of the present invention, the projections on the thread member are tapered from a larger transverse dimension down towards an end of the thread member opposite the connector element, while the thread member, the loop member, the connector element and the locking component or components are integrally molded. Advantageously, a needle element is attached to the thread member at an end thereof opposite the connector element.

A suture device in accordance with the present invention may be understood as having a body member which defines the aperture for receiving the thread member. According to this conceptualization of the invention, the thread member is connected to one side of the body member, while the loop member is connected to another side of the body member substantially opposite the thread member. In addition, the body member is provided with an access channel extending between the loop member and the aperture and is further provided with the locking component or components for preventing a removal of the thread member from the aperture upon a threading of the thread member through the loop member and a subsequent pulling of the thread member through the access channel into the aperture from the loop member.

A suture device in accordance with the present invention is easy to use, particularly in cases requiring a small sutures or ligatures. The suture device may in such cases comprise a comparatively small amount of material. And such a suture device can be used in both ligating and suturing operations, in microsurgery and possibly neurosurgery, as well as in more conventional applications such as ligation of blood vessels and other ducts and approximation of ribs and the binding of sternums.

A suture device in accordance with the present invention provides a suture which is virtually slippage free, even in cases where considerable amounts of stress and tension are involved. Such a suture device enables or at least facilitates the application of higher magnitudes of force to provide tighter bonds, closures and ligations.

BRIEF DESCRIPTION OF THE DRAWING

FIG. 1 is a side elevational view of a suture device in accordance with the present invention.

FIG. 2 is a side elevational view of another suture device similar but not identical to the suture device of FIG. 1.

DETAILED DESCRIPTION

Figure 3:
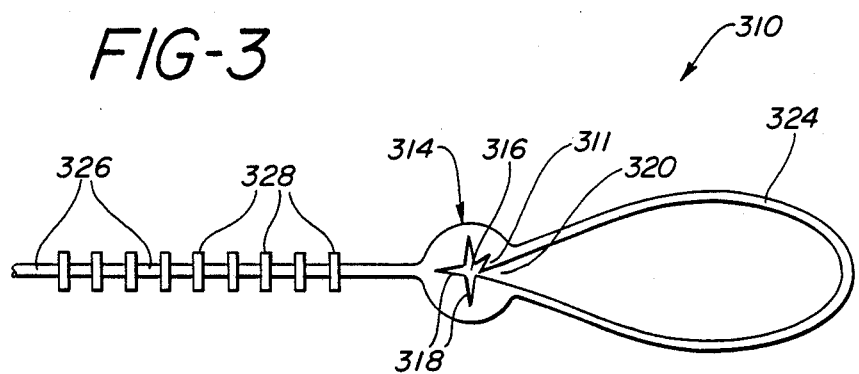
FIG. 3 is a partial side elevational view, on an enlarged scale, of another suture device in accordance with the present invention.

As illustrated in FIG. 1, a suture device 110 comprises a thread member 126, a loop member 124, a connector element 114, and a locking mechanism in the form of a pair of inwardly projecting resilient protuberances 111 and 113 on loop member 114. Thread member 126 is formed along a portion of its length with a series of conically tapering projections 128 and has an outer diameter D1 defined by a maximum outer transverse dimension of projections 128. Projections 128 each taper from the maximum outer transverse dimension on a side facing connector element 114 to a minimum traverse dimension at the adjacent projection.

Loop member 124 defines an opening 115 having an effective linear dimension or overall diameter D2 (when the loop is circularly arranged) substantially larger than, i.e., at least two times as large as, outer diameter D1 of thread member 126. Connector element 114 is in the shape of a Y and serves to couple one end of thread member 126 to loop member 124. Loop member 124, connector element 114 and protuberances 111 and 113 define a generally triangular aperture 116 having a linear dimension or size smaller than outer diameter D1 of thread member 126. Generally, aperture 116 has an area smaller than the cross-sectional area of projections 128 at the large ends thereof.

Protuberances 111 and 113 define a passageway or access channel 120 between opening 115 and aperture 116. The protuberances serve to prevent a removal of thread member 126 from aperture 116 upon a passing of thread member 126 through opening 115 (i.e., through loop member 124) and a subsequent pulling of thread member 126 into aperture 116 from opening 115 through access channel 120.

It is to be noted that connector element 114 and protuberances 111 and 113 may be considered to form a body member to which thread member 126 on one side and loop member 124 on an opposite side are connected. Aperture 116 is provided in the body member.

As illustrated in FIG. 2, another suture device 210 similar to that illustrated in FIG. 1, also comprises a thread member 226, a loop member 224, a connector element 214, and a locking mechanism in the form of a pair of inwardly projecting resilient protuberances 211 and 213 on loop member 214. Thread member 226 is formed along a portion of its length with a series of conically tapering projections 228 and has an outer diameter D21 defined by a maximum outer transverse dimension of projections 228. Projections 228 each taper from the maximum outer transverse dimension on a side facing connector element 214 to a minimum traverse dimension on an opposite side.

Loop member 224 defines an opening 215 having an effective linear dimension or overall diameter D22 (when the loop is in a circular configuration) substantially larger than, i.e., at least two times as large as, outer diameter D21 of thread member 226. Connector element 214 is in the shape of a Y and serves to couple one end of thread member 226 to loop member 224. Loop member 224, connector element 214 and protuberances 211 and 213 define a generally triangular aperture 216 having a linear dimension or size smaller than outer diameter D21 of thread member 226. Generally, aperture 216 has an area smaller than the cross-sectional area of projections 228 at the large ends thereof.

Protuberances 211 and 213 define a passageway or access channel 220 between opening 215 and aperture 216. The protuberances serve to prevent a removal of thread member 226 from aperture 216 upon a passing of thread member 226 through opening 215 (i.e., through loop member 224) and a subsequent pulling of thread member 226 into aperture 216 from opening 215 through access channel 220.

It is to be noted that connector element 214 and protuberances 211 and 213 may be considered to form a body member to which thread member 226 on one side and loop member 224 on an opposite side are connected.

Suture device 210 differs from suture device 110 in several respects. The free end of thread member 226 is provided with a hook shaped suture needle 232, and loop member 224 is smaller than loop member 224. In addition, loop member 224 is provided on a side opposite connector element 214 with an extension thread 230, for purposes of facilitating the manipulation of loop 224 by a surgeon or other user, so that loop 224 may be held outwardly to enable easy passage of thread member 226 through opening 215. Finally, projections 228 are at least partially hollow, while projections 128 are substantially solid.

As depicted in FIG. 3, a suture device 310 comprises a body member 314 generally in the form of a small cylinder or sphere. Body member 314 is provided with a star-shaped aperture or bore 316 extending longitudinally (or diametrically, in the case of a sphere) through the body member and provided with a plurality of circumferentially or angularly spaced tapering fingers 318. One finger 320 forms an access channel extending to an opening 315 defined in a loop 326 attached to body member 314 Along access channel 320 body member 314 is provided with a resilient inwardly projecting protuberance 311.

Suture device 310 also comprises a thread 326 attached to the outer surface of body member 314 on a side thereof opposite access channel 320. The other end of thread 324 is unattached, i.e., a free end.

Thread member 326 is provided along at least a portion of its length with a multiplicity of substantially equispaced ribs 328. Ribs 328 have an outer diameter substantially smaller than a linear dimension or diameter of opening 315, whereby thread member 326 with ribs 328 easily passes through opening 315.

Protuberance 311 serves to prevent a removal of thread member 326 from aperture 316 upon a passing of thread member 326 through opening 315 (i.e., through loop member 324) and a subsequent pulling of thread member 326 into aperture 316 from opening 315 through access channel 320.

It is to be noted that connector element 314 and protuberances 311 and 313 may be considered to form a body member to which thread member 326 on one side and loop member 324 on an opposite side are connected.

Figure 4:
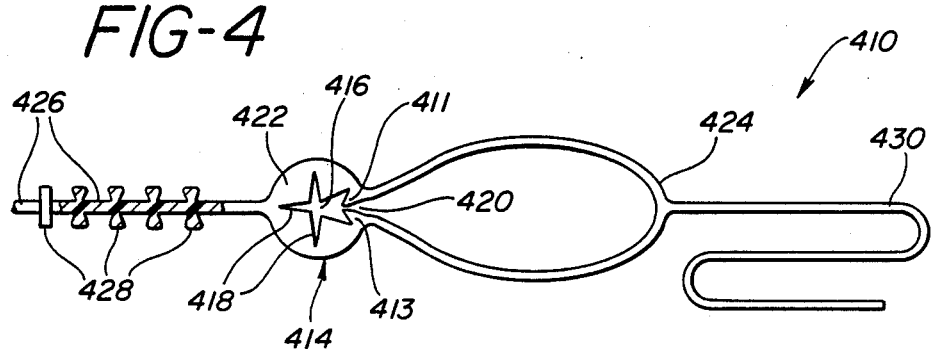
FIG. 4 is a partial side elevational view, on an enlarged scale, of yet another suture device in accordance with the present invention.

FIG. 4 depicts a suture device 410 similar to suture device 310, insofar as suture device 410 also comprises a body member 414 generally in the form of a small synthetic resin or polymeric cylinder. Body member 414 is formed with a star-shaped aperture or bore 416 having several tapering fingers 418. One finger 420 is open on an outer side and extends to an outer surface 422 of body member 414. Suture device 410 also comprises a first thread 424 and a second thread 426. First thread 424 is attached at its opposite ends to outer surface 422 on opposite side of finger 420 to form a loop, while one end of second thread 426 is connected to body member 414 on a side thereof opposite finger 420. Thread 424 is provided along at least a portion of its length with a multiplicity of flattened, tire shaped ribs 428.

As depicted in FIGS. 3 and 4, the loop formed by thread 424 of suture device 410 is smaller than loop 324 of suture device 310. In addition, thread 424 is connected at a point approximately midway along its length to one end of a third thread 430. The other end of thread 430 is free Body member 414 is provided along finger 420 with a pair of resilient inwardly projecting protuberances 411 and 413 which serve to prevent a removal of thread member 426 from aperture 416 upon a passing of thread member 426 through an opening 415 defined by thread 424 and upon a subsequently pulling of thread member 426 into aperture 416 from opening 415 through finger 420.

Figure 5:
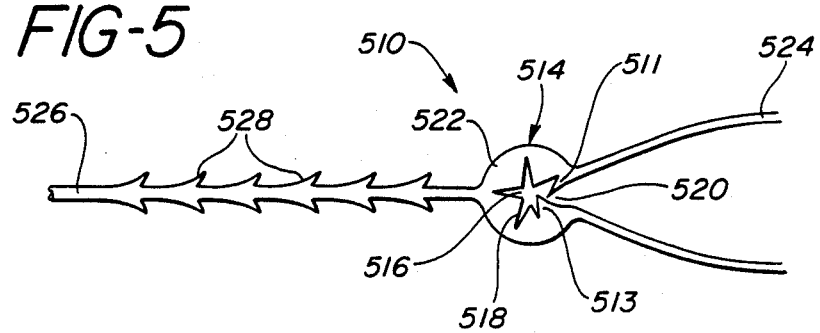
FIGS. 5 and 6 are partial side elevational views of additional suture devices in accordance with the present invention.

As illustrated in FIG. 5, a suture device 510 comprises a body member 514 generally in the form of a small cylinder or sphere. Body member 514 is provided with a star-shaped aperture or bore 516 extending longitudinally (or diametrically, in the case of a sphere) through the body member and provided with a plurality of circumferentially or angularly spaced tapering fingers 518. One finger 520 extends to an outer surface 522 of body member 514.

Suture device 510 also comprises a first thread 524 attached at its opposite ends to outer surface 522 on opposite side of finger 520 to form a loop defining an opening 515. One end of a second thread 526 is attached to outer surface 522 of body member 514 on a side thereof opposite finger 520. The other end of thread 524 is unattached.

Thread 524 is provided along at least a portion of its length with a multiplicity of barbs, teeth or serrations 528 which are inclined from the free end of thread 526 towards the attached end thereof, i.e., towards body member 514.

Body member 514 is provided along finger 520 with a pair of resilient protuberances 511 and 513 projecting inwardly towards aperture or bore 516. Protuberances 511 and 513 are staggered with respect to one another, protuberance 513 being closer than protuberance 511 to the center of aperture 516. Protuberances 511 and 513 serve the locking or blocking function described above.

Figure 6:
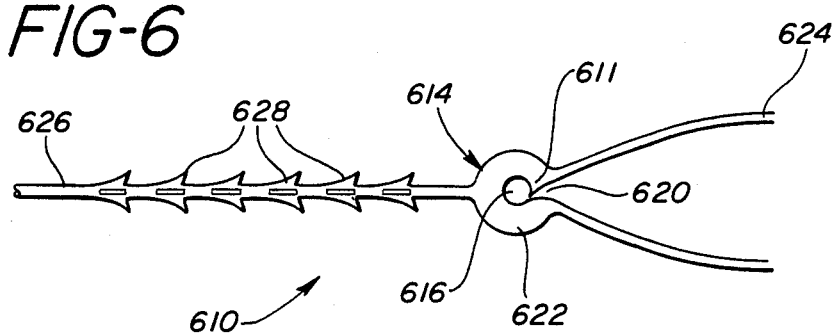

As illustrated in FIG. 6, another suture device 610 in accordance with the invention includes a body member 614 with a substantially cylindrical aperture 616 communicating via a passageway or access channel 620 with a loop formed by a thread 624 attached at its ends to an outer surface 622 of body member 614 on opposite sides of channel 620. A thread 626 is connected at one end to body member 614 on a side thereof opposite channel 620 and thread 624. Thread 626 is provided along at least a portion of its length with a multiplicity of barbs, teeth or serrations 628 which are inclined outwardly from the free end of thread 626 towards body member 614. Teeth 628 are triangular and are provided in longitudinally spaced arrays of four circumferentially spaced teeth.

Body member 610 is provided in channel 620 with an inwardly directed barb, hook or fingerlike protuberance 211 which overlaps the inner end of channel 620 and acts as a one-way valve member to close that channel to the removal of thread 624 upon the lodgement thereof in aperture 616.

Figure 7:
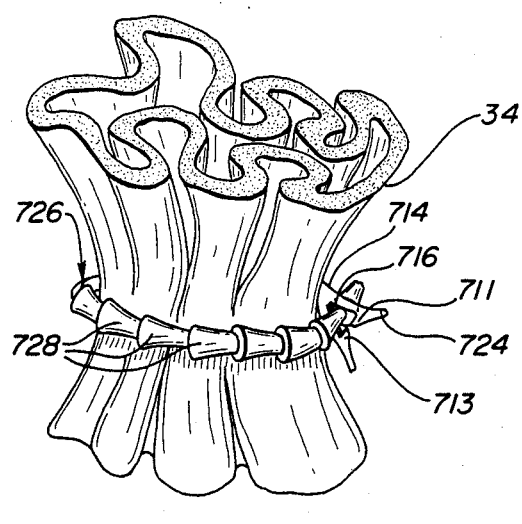
FIG. 7 is a perspective view, on an enlarged scale, of another embodiment of a suture device in accordance with the present invention, upon use thereof in ligating a blood vessel.

FIG. 7 illustrates the disposition of a suture device 710 (basically the same as suture devices 110 and 210) with respect to a blood vessel 34 upon the completion of an operation attaching the suture device to the vessel to close it. Suture device 710 includes a thread 726 provided along at least a portion of its length with a series of conically tapered projections 728. Thread 726 extends from a Y-shaped body member 714 around the circumference of vessel 34 and through a triangular aperture 716 in the body member. A free end of thread 726 is locked to body member 714 in part by a pair of protuberances 711 and 713 incorporated in body member 714. Protuberances 711 and 713 are resilient finger shaped elements defining an access channel (not designated) communicating with aperture 716 and serving to enable a surgeon to slip thread 726 into the aperture and to prevent the thread from slipping out of the aperture back through the access channel. The free end of thread 726 is also locked to body member 714 because projections 728 are too large, at their wide ends, to pass back through aperture 716. A loop 724 connected to body member 714 and the free end of thread 726 extending beyond body member 714 are severed near body member 714.

Figure 8A:
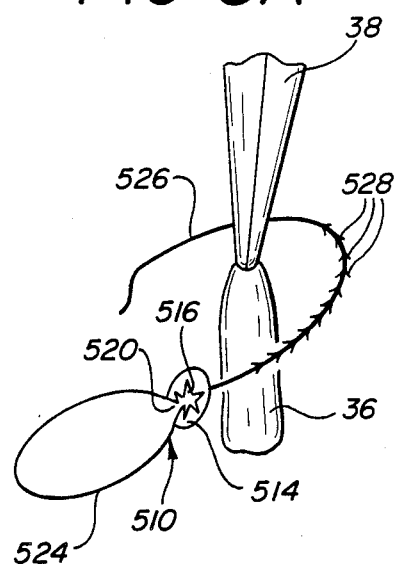
FIGS. 8A through 8D are schematic perspective views showing successive steps in using a suture device in accordance with the present invention, for ligating a vessel or duct.
Figure 8B:
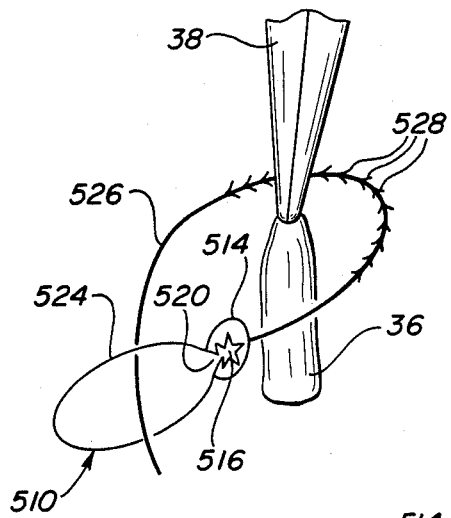
Figure 8C:
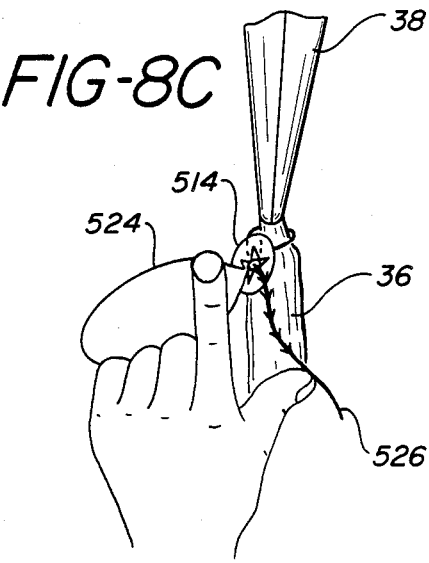
Figure 8D:
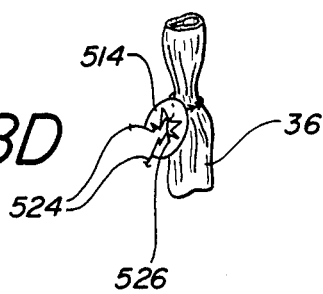

The attachment of suture device 510 to an open blood vessel 36 or other tubular duct is schematically shown in FIGS. 8A through 8D. The open end of vessel 36 is first clamped by a hemostat 38 or other surgical instrument. Upon a placement of device 510 proximately to vessel 36, as illustrated in FIG. 8A, the free end of thread 526 is passed around the vessel. As shown in FIG. 8B, the free end of thread 526 is then passed through through loop 524. As the loop consequently formed by thread 526 is closed about blood vessel 36, care being taken to ensure the proper disposition of the loop about the end of the vessel, thread 526 is slipped through open finger or passageway 520 into bore 516. With the surgeon holding suture device 510 in place, as schematically indicated in FIG. 8C, thread 526 is pulled longitudinally through bore 516 until the loop formed by the thread has tightened sufficiently to close off and clamp blood vessel 36. As described above, serrations 528 function to prevent thread 526 from slipping back through bore 516 and to thereby lock the suture device around blood vessel 36. Upon the completion of the loop tightening operation, thread 526, as well as thread 524, is severed at a point near body member 514, as shown in FIG. 8D. Hemostat 38 may then be removed from the end of the clamped vessel.

Figure 9A:
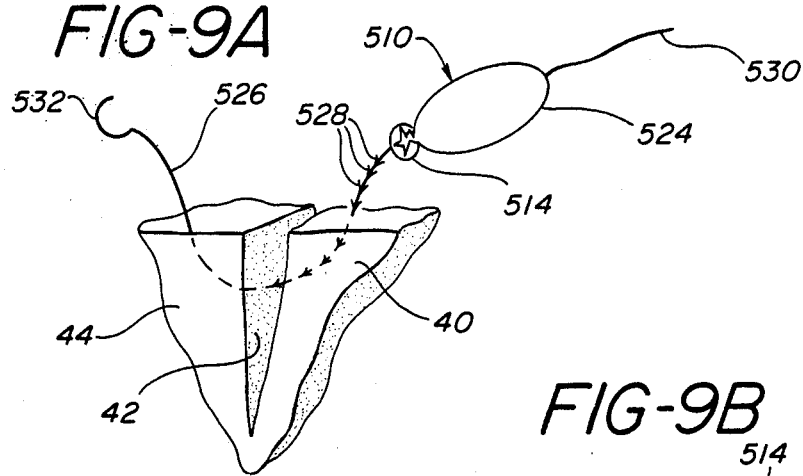
FIGS. 9A through 9D are schematic perspective views showing successive steps in using a suture device in accordance with the present invention, for closing a wound or cut in a body tissue or organ.
Figure 9B:
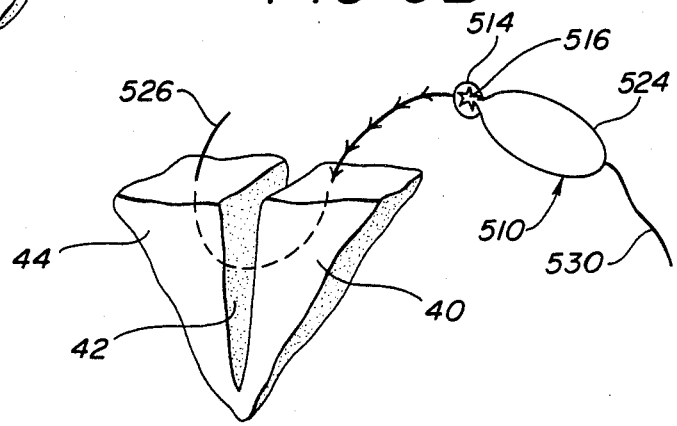
Figure 9C:
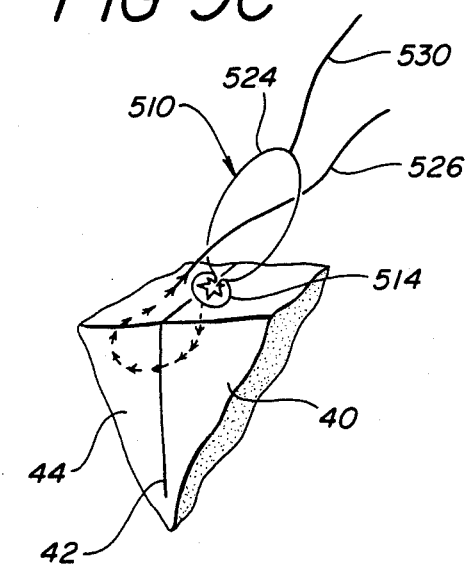
Figure 9D:
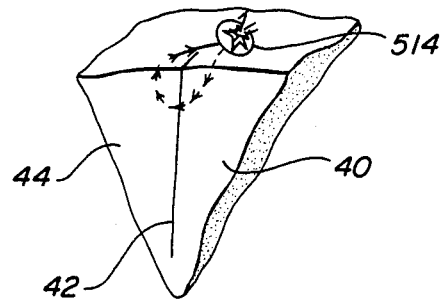

The use of suture device 510 to close an open cut 42 is schematically depicted in FIGS. 9A through 9D. Upon a placement of device 510 proximately to body tissues 40 near cut 42, as illustrated in FIG. 9A, the free end of thread 526 is passed through tissues 40, cut 42 and tissues 44 on the other side of the cut. To facilitate this sewing operation, the free end of thread 526 is provided with a relatively inflexible extension 132 in the form of a hook-shaped needle 532. As shown in FIG. 9B, needle extension 532 is removed or cut from thread 526 upon the passage of the thread through tissue portion 44. Subsequently, the free end of thread 526 is passed through loop 524, as shown in FIG. 9C. As a loop consequently formed by thread 526 is closed, thereby drawing tissue portions 40 and 44 towards one another to close cut 42, thread 526 is slipped through open finger or passageway 520 into bore 516. Thread 526 is then pulled longitudinally through bore 516 until the loop formed by thread 526 has tightened to close cut 42 and clamp tissue portions 40 and 42 to one another. As described above, serrations 528 function to prevent thread 526 from slipping back through bore 516 and lock the suture device in a clamping configuration to the body tissues. Upon the tightening of thread 526, that thread, as well as thread 524, is severed at a point near body member 514, as shown in FIG. 9D.

It is to be noted that protuberances 511 and 513 have been omitted from FIGS. 8A–8D and 9A–9D for purposes of simplifying the drawing. In addition, FIGS. 9A–9C show surgical device 510 with an extension 530 on loop 524. Thread 530 serves to facilitate the handling of loop 524 in cases where loop 524 is too small to conveniently manipulate while passing thread 526 therethrough. It is to be further understood that any of the particular embodiments of a suture device described herein may be used in performing the surgical operations described with reference to FIGS. 8A–8D and 9A–9D above.

The suture devices described herein are all integrally molded pursuant to techniques well known in the art. The sutures are made of polyethylene, polypropylene, nylon, tetrafluoroethylene or other synthetic resin or polymeric material which is essentially inert and therefore biochemically safe for sustained contact with the body tissues of human beings and other animals. The suture needles are attached to the free ends of the thread members by embedding techniques also well known in the art.

Suture devices in accordance with the present invention can be used controlling bleeding vessels, tying off open ducts (e.g., bile ducts), creating anastomoses (connecting the open ends of two tubular sections in a splicing type operation), and suturing together flaps of skin or other body tissues on opposite sides of a cut. Suture devices as described herein, if appropriately dimensioned, can be used in microsurgery and neurosurgery and for such larger scale operations as binding sternums and approximating ribs.

Although the invention has been described in terms of particular embodiments and applications, one of ordinary skill in the art, in light of this teaching, can generate additional embodiments and modifications without departing from the spirit of or exceeding the scope of the claimed invention. Accordingly it is to be understood that the drawings and descriptions herein are preferred by way of example to facilitate comprehension of the invention and should not be construed to limit the scope thereof.

What is claimed is:

1. A suture device comprising:
a thread member provided along at least a portion of its length with a series of resilient projections, said thread member having an outer diameter defined by said projections;
a loop member defining an opening having a linear dimension at least two times as large as said outer diameter; and
joining means for connecting one end of said thread member to said loop member, at least one of said joining means and said loop member defining at least in part an aperture having a linear dimension smaller than said outer diameter, said aperture communicating with said opening defined by said loop; and
locking means, provided on at least one of said joining means and said loop member, for preventing a removal of said thread member from said aperture upon a passing of said thread member through said loop member and a subsequent pulling of said thread member into said aperture from said loop member.

2. The suture device set forth in claim 1 wherein said locking means includes at least one protuberance on said loop.

3. The suture device set forth in claim 2 wherein said protuberance projects towards said aperture.

4. The suture device set forth in claim 1 wherein said locking means includes two protuberances projecting from said loop towards said aperture.

5. The suture device set forth in claim 1 wherein said joining means comprises a Y-shaped connector piece between said one end of said thread member and said loop member.

6. The suture device set forth in claim 1 wherein said loop member is provided on a side opposite said joining means and said thread member with an additional member extending away from said loop member.

7. The suture device set forth in claim 6 wherein said additional member takes the form of an additional thread member.

8. The suture device set forth in claim 1, further comprising a needle element attached to said thread member, at an end thereof opposite said joining means.

9. The suture device set forth in claim 1 wherein said joining means comprises a body member between said loop member and said thread member, said body member being formed with said aperture.

10. The suture device set forth in claim 9 wherein said body member is cylindrical.

11. The suture device set forth in claim 1 wherein said aperture is star-shaped.

12. The suture device set forth in claim 1 wherein said projections are tapered from a larger transverse dimension down towards an end of said thread member opposite said joining means.

13. The suture device set forth in claim 1 wherein said thread member, said loop member, said joining means and said locking means are integrally molded.

14. A suture device comprising:
a thread member provided along at least a portion of its length with a series of resilient projections, said thread member having an outer diameter defined by said projections;
a loop member defining an opening having a linear dimension at least two times as large as said outer diameter; and
a body member defining an aperture having a linear dimension smaller than said outer diameter, one end of said thread member being connected to one side of said body member, said loop member being connected to another side of said body member substantially opposite said one side, said body member being provided with an access channel extending between said loop member and said aperture, said body member being further provided with locking means for preventing a removal of said thread member from said aperture upon a threading of said thread member through said loop member and a subsequent pulling of said thread member through said access channel into said aperture from said loop member.

15. The suture device set forth in claim 14 wherein said locking means includes at least one protuberance, said access channel being defined at least in part by said protuberance.

16. The suture device set forth in claim 15 wherein said aperture is generally triangular.

17. The suture device set forth in claim 15 wherein said locking means includes two protuberances, said access channel passing between said protuberances.

18. The suture device set forth in claim 15 wherein said body member is essentially Y-shaped.

19. The suture device set forth in claim 15 wherein said loop member is provided on a side opposite said body member with an additional member extending away from said loop member.

20. The suture device set forth in claim 19 wherein said additional member takes the form of an additional thread member.

21. The suture device set forth in claim 15 wherein said aperture is generally triangular.

22. The suture device set forth in claim 15, further comprising a needle element attached to said thread member at an end thereof opposite said joining means.

23. The suture device set forth in claim 15 wherein said body member is cylindrical.

24. The suture device set forth in claim 15 wherein said aperture is star-shaped.

25. The suture device set forth in claim 15 wherein said projections are tapered from a larger transverse dimension down towards an end of said thread member opposite said joining means.

26. A method for binding a wound in a patient, comprising the steps of:
providing a suture device having:
a thread member provided along at least a portion of its length with a series of resilient projections, said thread member having an outer diameter defined by said projections;
a loop member defining an opening having a linear dimension substantially larger than said outer diameter; and
a body member defining an aperture having a linear dimension smaller than said outer diameter, one end of said thread member being connected to one side of said body member, said loop member being connected to another side of said body member substantially opposite said one side, said body member being provided with an access channel extending between said loop member and said aperture, said body member being further provided with locking means for preventing a removal of said thread member from said aperture upon a threading of said thread member through said loop member and a subsequent pulling of said thread member through said access channel into said aperture from said loop member;

passing a free end of said thread member through or around a body tissue or organ to be tied;

subsequently passing said free end of said thread through said loop member so that said thread member forms another loop about the body tissue or organ to be tied;

pulling said thread member through said locking means into said aperture and so that said other loop decreases in size;

continuing to pull said thread member through said aperture to tighten said other loop at least partially about said body tissue or organ to be tied;

cutting a free end portion of said thread member upon a completing of the pulling operation; and severing said loop member from said joining means upon a completing of the pulling operation.

* * * * *